US006251303B1

(12) United States Patent
Bawendi et al.

(10) Patent No.: US 6,251,303 B1
(45) Date of Patent: Jun. 26, 2001

(54) WATER-SOLUBLE FLUORESCENT NANOCRYSTALS

(75) Inventors: Moungi G. Bawendi, Boston; Frederick V. Mikulec, Somerville, both of MA (US); Jin-Kyu Lee, Seoul (KR)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/156,863

(22) Filed: Sep. 18, 1998

(51) Int. Cl.[7] ................................................... C09K 11/02
(52) U.S. Cl. ........................... 252/301.4 R; 252/301.4 S; 252/301.6 R; 252/301.6 S; 428/690; 428/403; 428/407
(58) Field of Search .................... 428/403, 407, 428/690; 252/301.4 R, 301.4 S, 301.6 R, 301.6 S

(56) References Cited

U.S. PATENT DOCUMENTS

| | | | |
|---|---|---|---|
| 3,996,345 | 12/1976 | Ullman et al. | 424/12 |
| 4,637,988 | 1/1987 | Hinshaw et al. | 436/546 |
| 4,777,128 | 10/1988 | Lippa | 435/5 |
| 5,262,357 | 11/1993 | Alivisatos et al. | 437/233 |
| 5,293,050 | 3/1994 | Chapple-Sokol et al. | 257/17 |
| 5,304,786 | 4/1994 | Pavlidis et al. | 235/462 |
| 5,354,707 | 10/1994 | Chapple-Sokol et al. | 437/106 |
| 5,395,791 | 3/1995 | Cheng et al. | 437/105 |
| 5,422,489 | 6/1995 | Bhargava | 250/488.1 |
| 5,492,080 | 2/1996 | Ohkawa et al. | 117/108 |
| 5,499,260 | 3/1996 | Takahashi et al. | 372/46 |
| 5,505,928 | 4/1996 | Alivisatos et al. | 423/299 |
| 5,515,393 | 5/1996 | Okuyama et al. | 372/45 |
| 5,525,377 | 6/1996 | Gallagher et al. | 427/512 |
| 5,537,000 | 7/1996 | Alivisatos et al. | 313/506 |

(List continued on next page.)

FOREIGN PATENT DOCUMENTS

| | | |
|---|---|---|
| WO 95/29473 | 11/1995 | (WO) . |
| WO 98/04740 | 2/1998 | (WO) . |
| 98/19963 | 5/1998 | (WO) . |
| WO 98/33070 | 7/1998 | (WO) . |
| WO 98/36376 | 8/1998 | (WO) . |

OTHER PUBLICATIONS

Milkulec et al, "Fluorescent Semiconductor Nanocrystallites Derivatized With Biomolecules", Aug. 24, 1998, Amer. Chem. Soc. Nat'l Meeting.*

Alivisatos et al., "Semiconductor Clusters, Nanocrystals, and Quantum Dots," *Science,* 271:933–937, 1996.

Alivisatos et al., "Organization of 'nanocrystal molecules' using DNA," *Nature,* 382:609–611, Aug. 15, 1996.

Baldwin et al., "Synthesis of a Small Molecule Combinatorial Library Encoded with Molecular Tags," *J. Am. Chem. Soc.,* 117:5588–5589, May 24, 1995.

(List continued on next page.)

*Primary Examiner*—C. Melissa Koslow
(74) *Attorney, Agent, or Firm*—Fish & Richardson P.C.

(57) ABSTRACT

A water soluble semiconductor nanocrystal capable of light emission is provided, including a quantum dot having a selected band gap energy, a layer overcoating the quantum dot, the overcoating layer comprised of a material having a band gap energy greater than that of the quantum dot, and an organic outer layer, the organic layer comprising a compound having at least one linking group for attachment of the compound to the overcoating layer and at least one hydrophilic group spaced apart from the linking group by a hydrophobic region sufficient to prevent electron charge transfer across the hydrophobic region. The particle size of the nanocrystal core is in the range of about 12 Å to about 150 Å, with a deviation of less than 10% in the core. The coated nanocrystal exhibits photoluminescence having quantum yields of greater than 10% in water.

43 Claims, 7 Drawing Sheets

U.S. PATENT DOCUMENTS

| | | | |
|---|---|---|---|
| 5,541,948 | 7/1996 | Krupke et al. | 372/41 |
| 5,565,324 | 10/1996 | Still et al. | 435/6 |
| 5,585,640 | 12/1996 | Huston et al. | 250/483.1 |
| 5,625,456 | 4/1997 | Lawandy | 356/376 |
| 5,674,698 | 10/1997 | Zarling et al. | 435/7.92 |
| 5,721,099 | 2/1998 | Still et al. | 435/6 |
| 5,736,330 | 4/1998 | Fulton | 435/6 |
| 5,747,180 | 5/1998 | Miller et al. | 372/41 |
| 5,751,018 * | 5/1998 | Alivisatos et al. | 257/64 |
| 5,770,299 | 6/1998 | Dannenhauer et al. | 428/195 |
| 5,789,162 | 8/1998 | Dower et al. | 435/6 |
| 5,985,173 * | 11/1999 | Grey et al. | 252/301.4 R |
| 5,985,353 | 11/1999 | Lawton et al. | 427/2.13 |
| 5,990,479 | 11/1999 | Weiss et al. | 250/307 |

OTHER PUBLICATIONS

Bawendi et al., "Luminescence properties of CdSe quantum crystallites: resonance between interior and surface localized states," *J. Chem. Phys.,* 96(2):946–954, Jan. 15, 1992.

Beverloo et al., "Preparation and Microscopic Visualization of Multicolor Luminescent Immunophosphors," *Cytometry,* 13:561–570, 1992.

Bruchez et al., "Semiconductor Nanocrystals as Fluorescent Biological Labels," *Science,* 281:2013–2016, Sep. 25, 1998.

Bruchez et al., "Semiconductor nanocrystals as fluorescent piological for biology," *Cytometry,* Supplement 9, p. 26, Mar., 1998.

Chee et al., "Accessing Genetic Information with High–Density DNA Arrays," *Science,* 274(5287):610, Oct. 25, 1996.

Coffer et al., "Characterization of quantum–confined CdS nanocrystallites stabilized by deoxyribonucleic acid (DNA)," *Nanotechnology,* 3:69–76, 1992.

Colvin et al., "Light–emitting diodes made from cadmium selenide nanocrystals and a semiconducting polymer" *Nature,* 370(6488):354–357, Aug. 4, 1994.

Cook, "Scintillation Proximity Assay: A Versatile High–Throughput Screening Technology," *Drug Discovery Today,* 1:287–294, 1997.

Correa–Duarte et al., "Stabilization of CdS semiconductor nanoparticles against photodegradation by silica coating procedure," *Chem. Phys. Lett.,* 286:497–501, Apr. 17, 1998.

Czarnik, "Encoding methods for combinatorial chemistry," *Curr. Opin. Chem. Biol.,* 1(1):60, 1997.

Egner et al., "Tagging in combinatorial chemistry: the use of coloured and fluorescent beads," *Chem. Commun.,* 735–736, Apr. 21, 1997.

Fodor, "Techwire," *Science,* 277(5324):393–395, Jul. 18, 1997.

Gao et al., "Strongly Photoluminescent CdTe Nanocrystals by Proper Surface Modification," *J. Phys. Chem.,* 102:8360–8363, 1998.

Guha et al., "Hybrid organic–inorganic semiconductor––based light–emitting diodes," *J. Appl. Phys.,* 82(8):4126–4128, Oct. 15, 1997.

Jarvis et al., "Solution Synthesis and Photoluminescence Studies of Small Crystallites of Cadmium Telluride," *Mat. Res. Soc. Symp. Proc.,* 272:229–234, 1992.

Kagan et al., "Electronic Energy Transfer in CdSe Quantum Dot Solids," *Physical Review Letters,* 76:1517–1520, Feb. 26, 1996.

Kagan et al., "Long–range resonance transfer of electronic excitations in close–packed CdSe quantum–dot solids," *Physical Review Letters,* 54:8633–8643, Sep. 15, 1996.

Lee et al., "Surface Derivatization of Nanocrystalline CdSe Semiconductors," *Mat. Res. Soc. Symp. Proc.,* 452:323–328, 1997.

Mahtab et al., "Protein–sized quantum dot luminescence can distinguish between 'straight', 'bent', and 'kinked' oligonucletides", *J. Am. Chem. Soc.,* 117:9099–9100, Sep. 6, 1995.

Mahtab et al., "Preferential–absorption of a 'kinked' DNA to a newtral curved surface: comparison to and implications for nonspecific DNA–protein interactions," *J. Am. Chem. Soc.,* 118:7028–7032, Jul. 31, 1996.

McGall et al., "Light–directed synthesis of high–density oligonucleotide arrays using semiconductor photoresists," *Proc. Natl. Acad. Sci. USA,* 93:13555–13560, Nov., 1996.

Michael et al., "Randomly Ordered Addressable High–Density Optical Sensor Arrays," *Analytical Chemistry,* 70:1242–1248, Apr. 1, 1998.

Mikulec et al., "Synthesis and Characterization of Highly Luminescent (CdSe)ZnS Quantum Dots," *Materials Research Society Symposium,* 452:359–364, 1997.

Moran, "Radio Frequency Tag Encoded Combinatorial Library Method for the Discovery of Tripeptide–Substituted Cinnamic Acid Inhibitors of the Protein Tyrosine Phosphatase PTP1B," *J. Am. Chem. Soc.,* 117:10787–10788, 1995.

Müllenborn et al., "Characterization of Solution–Synthesized CdTe and HgTe," *Applied Physics,* 56:317–321, 1993.

Murphy et al., "Quantum dots as inorganic DNA–binding proteins," *Mat. Res. Soc. Symp.,* 452:597–600, 1997.

Nicolau et al., "Radiofrequency Encoded Combinatorial Chemistry," *Ingew. Chem. Int. Ed. Engl.,* 34(20):2289–2291, 1995.

Pehnt et al., "Nanoparticle Precursor Route to Low–Temperature Spray Deposition of CdTe Thin Films," *Appl. Phys. Lett.,* 67(15):2176–2178, Oct. 9, 1995.

Peng et al., "Epitaxial Growth of Highly Luminescent CdSe/CdS Core/Shell Nanocrystals with Photostability and Electronic Accessibility," *J. Am. Chem. Soc.,* 119:7019–7029, Jul. 30, 1997.

Peng et al., "Synthesis and Isolation of a Homodimer of Cadmium Selenide Nanocrystals," *Angewandte Chemie,* 36:145–147, Feb. 3, 1997.

Plunkett et al., "Combinatorial Chemistry and New Drugs," *Scientific American,* 276(4):68–73, Apr. 1997.

Schröck et al., "Multicolor Spectral Karyotyping of Human Chromosomes," *Science,* 273:494–497, Jul. 26, 1996.

Service, "Semiconductor Beacons Light Up Cell Structures," *Science,* 281:1930–1931, Sep. 25, 1998.

Steigerwald et al., "Surface Derivatization and Isolation of Semiconductor Cluster Molecules," *J. Am. Chem. Soc.,* 110:3046–3050, 1988.

Wade, "In the Hunt for Useful Genes, a Lot Depends on 'Snips'", *New York Times,* C1, C5, Aug. 11, 1998.

Wang et al., "Large–Scale Identification, Mapping and Genotyping of Single–Nucleotide Polymorphisms in the Human Genome," *Science,* 280:1077–1082, May 15, 1988.

Whitesell, "Directionally Aligned Helical Peptides on Surfaces", *Science,* 261:73–75, Jul. 2, 1993.

Winzeler et al., "Direct Allelic Variation Scanning of the Yeast Genome", *Science,* 281:1194–1197, Aug. 21, 1998.

Spanhel, et al., "Photochemistry of Colloidal Semiconductors. Surface Modification and Stability of Strong Luminescing CdS Particles," *J. Am. Chem. Soc.* 109(19):5649–5655, 1987.

Kortan, et al., "Nucleation and Growth of CdSe on ZnS Quantum Crystallite Seeds, and Vice Versa, in Inverse Micelle Media," *J. Am. Chem. Soc.* 112:1327–1332, 1990.

Murray, et al., "Synthesis and Characterization of Nearly Monodisperse CdE (E=S, Se, Te) Semiconductor Nanocrystallites," *J. Am. Chem. Soc.* 115(19):8706–8715, 1993.

Rajh, et al., "Synthesis and Characterization of Surface–Modified Colloidal CdTe Quantum Dots," *J. Phys. Chem.* 97:111999–12003, Nov. 1993.

Lawless, et al., "Bifunctional Capping of CdS Nanoparticles and Bridging to TiO2," *J. Phys. Chem.* 99:10329–10335, 1995.

Dabbousi, et al., "Electroluminescence from CdSe quantum–dot/polymer composites," *Appl. Phys. Lett* 66(11):1316–1318, Mar. 13, 1995.

Alivisatos, "Perspectives on the Physical Chemistry of Semiconductor Nanocrystals," *J. Phys. Chem.* 1996(100):13226–13239, 1996.

Danek, et al., "Synthesis of Luminescent Thin–Film CdSe/ZnSe Quantum Dot Composites Using CdSe Quantum Dots Passivated with an Overlayer of ZnSe," *Chem. Mater.* 8(1):173–180, 1996.

Liz–Marzan, et al., "Synthesis of Nanosized Gold–Silica Core–Shell Particles," *Langmuir* 12:4329–4335, 1996.

Matsumoto, et al., "Preparation of Monodisperse CdS Nanocrystals by Size Selective Photocorrosion," *J. Phys. Chem* 100(32):13781–13785, 1996.

Rogach, et al., "Synthesis and Characterization of Thiol–Stabilized CdTe Nanocrystals," *Ber. Bunsenges. Phys. Chem.* 100(11):1772–2778, 1996.

Hines, et al., "Synthesis and Characterization of Strongly Luminescing ZnS–Capped CdSe Nanocrystals," *J. Phys. Chem.* 100:468–471, Jan. 1996.

Empedocles, et al., "Photoluminescence Spectroscopy of Single CdSe Nanocrystallite Quantum Dots," *Phys. Rev. Lett.* 77(18):3873–3876, Oct. 1996.

Nirmal, et al., "Fluorescence Intermittency in single Cadmium Selenide Nanocrystals," *Nature* 383:802–804, Oct. 1996.

Gan, et al., "Enhanced Photoluminescence and Characterization of Mn–Doped ZnS Nanocrystallites Synthesized in Microemulsion," *Langmuir* 1997(13):6427–6431, 1997.

Empedocles, et al., "Quantum–Confined Stark Effect in Single CdSe Nanocrystallite Quantum Dots," *Science* 278:2114–2117, Dec. 1997.

Kuno, et al., "The band edge luminescence of surface modified CdSe nanocrystallites: Probing the luminescing state," *J. Chem. Phys.* 106(23):9869–9882, Jun. 1997.

Dabbousi, et al., "(CdSe)ZnS core–shell quantum dots: synthesis and characterization of a size series of highly luminescent nanocrystallites," *J. of Phys. Chem. B* 101(46):9643–9475, Nov. 13, 1997.

Fox, et al., "Fluorescence and Redox Activity of Probes Anchored through an Aminotrithiol to Polycrystalline Gold," *Langmuir* 14:816–820, 1998.

Mikulec, et al., "Fluorescent semiconductor nanocrystallites derivatized with biomolecules," Amer. Chem. Soc. Nat'l Meeting, Boston, MA, Aug. 24, 1998.

Lett, "Color–Coding Quantum Dots Debut With Promising Careers In Clinical Diagnostics Field," :1–2, Sep. 25, 1998.

* cited by examiner

WATER-SOLUBLE FLUORESCENT NANOCRYSTALS

This application is related to the following applications which were filed in even date herewith and which are incorporated in their entirety by reference: applications entitled "Inventory Control" Ser. No. 60/101,046 filed Sep. 18, 1998, "Detection of Compounds and Interactions in Biological Systems Using Quantum Dots", Ser. No. 60/100, 947 filed Sep. 18, 1998.

FIELD OF THE INVENTION

This invention relates to water-soluble nanocrystalline materials that emit energy over a narrow range of wavelengths. In particular, the invention relates to water-soluble nanocrystals that emit light in the visible energy range.

BACKGROUND OF THE INVENTION

Semiconductor nanocrystals (quantum dots) whose radii are smaller than the bulk exciton Bohr radius constitute a class of materials intermediate between molecular and bulk forms of matter. Quantum confinement of both the electron and hole in all three dimensions leads to an increase in the effective band gap of the material with decreasing crystallite size. Consequently, both the optical absorption and emission of quantum dots shift to the blue (higher energies) as the size of the dots gets smaller.

Bawendi and co-workers have described a method of preparing monodisperse semiconductor nanocrystals by pyrolysis of organometallic reagents injected into a hot coordinating solvent (*J. Am. Chem. Soc.*, 115:8706 (1993)). This permits temporally discrete nucleation and results in the controlled growth of macroscopic quantities of nanocrystals. Size selective precipitation of the crystallites from the growth solution can provides crystallites with even narrower size distributions. The narrow size distribution of the quantum dots allows the possibility of light emission in narrow spectral widths.

In an effort to improve the photoluminescent yield of the quantum dots, the nanocrystal surface has been passivated by reaction of the surface atoms of the quantum dots with organic passivating ligands, so as to eliminate energy levels at the surface of the crystallite which lie within the energetically forbidden gap of the bulk interior. These surface energy states act as traps for electrons and holes which degrade the luminescence properties of the material. Such passivation produces an atomically abrupt increase in the chemical potential at the interface of the semiconductor and passivating layer (See, A. P. Alivisatos, *J. Phys. Chem.* 100:13226 (1996)). Bawendi et al. (*J. Am. Chem. Soc.* 115:8706 (1993)) describe CdSe nanocrystals capped with organic moieties such as tri-n-octyl phosphine (TOP) and tri-n-octyl phosphine oxide (TOPO) with quantum yields as high as 20% in organic solvents such as toluene. See also, thesis of Christopher Murray, "Synthesis and Characterization of II-VI Quantum Dots and Their Assembly into 3-D Quantum Dot Superlattices", Massachusetts Institute of Technology, September, 1995; and Kuno et al. (*J. Phys. Chem.* 106(23):9869 (June, 1997)).

Although semiconductor nanocrystals prepared as described by Bawendi and co-workers exhibit near monodispersity, and hence, high color selectivity, the luminescence properties of the material is process dependent. The stability of the photoluminescent property of the nanocrystal is a function of the nature of the passivating species coating the outer surface of the nanocrystal. Known organically coated nanocrystals are not robust and exhibit degradation of photoluminescent yield in solution. This is likely due to dissociation of the passivating layer from the surface of the quantum dot or degradation of the passivating layer resulting in degradation of the semiconductor surface.

Passivation of quantum dots using inorganic materials also has been reported. Particles passivated with an inorganic coating are more robust than organically passivated dots and have greater tolerance to processing conditions necessary for their incorporation into devices. Previously reported inorganically passivated quantum dot structures include CdS-capped CdSe and CdSe-capped CdS (Than et al., *J. Phys. Chem.* 100:8927 (1996)); ZnS grown on CdS (Youn et al., *J. Phys. Chem.* 92:6320 (1988)); ZnS on CdSe and the inverse structure (Kortan et al., *J. Am. Chem. Soc.* 112:1327 (1990)); ZnS-capped CdSe nanocrystals (M. A. Hines and P. Guyot-Sionnest, *J. Phys. Chem.* 100:468 (1996); ZnSe-capped CdSe nanocrystals (Danek et al., *Chem. Materials* 8:173 (1996) and $SiO_2$ on Si (Wilson et al., *Science* 262:1242 (1993)).

Kortan et al. describes a ZnS capped-CdSe quantum dot which has a layer of thiolphenyl groups bound to the outer surface. The thiolphenyl groups were used to passivate the surface and to allow the clusters to be isolated in powder form. Lawless et al. reported the preparation of CdS semiconductor nanocrystals capped with bifunctional mercaptocarboxylic acids $HS(CH_2)_nCOOH$, where n=1–3. $TiO_2$ particles were attached to the CdS dots through the functional carboxylic acid group of the bifunctional capping moiety in order to promote interparticle electron transfer between dissimilar semiconductor particles.

The quantum dots described above are soluble or dispersible only in organic solvents, such as hexane or pyridine. Many applications which rely on the fluorescent emission of the quantum dots require that the quantum dots be water-soluble.

Many reported water-soluble quantum dots suffer from significant disadvantages which limit their wide applicability. For example, Spanhel et al. discloses a $Cd(OH)_2$-capped CdS sol (*J. Am. Chem. Soc.* 109:5649 (1987)); however, the photoluminescent properties of the sol was pH dependent. The sol could be prepared only in a very narrow pH range (pH 8–10) and exhibited a narrow fluorescence band only at a pH of greater than 10. Such pH dependency greatly limits the usefulness of the material; in particular, it is not appropriate for use in biological systems.

Other groups have replaced the organic passivating layer of the quantum dot with water-soluble moieties; however, the resultant derivatized quantum dots are not highly luminescent. Short chain thiols such as 2-mercaptoethanol and 1-thio-glycerol have been used as stabilizers in the preparation of water-soluble CdTe nanocrystals. See, Rogach et al., *Ber. Bunsenges. Phys. Chem.* 100:1772 (November, 1996) and Rajh et al., *J. Phys. Chem.* 97:11999 (November 1993). Other more exotic capping compounds have been reported with similar results. See, Coffer et al. (*Nanotechnology* 3:69 (April, 1992) which describes the use of deoxyribonucleic acid (DNA) as a capping compound. In all of these systems, the coated quantum dots were not stable and photoluminescent properties degraded with time.

The unavailability of aqueous suspensions or solutions of quantum dots with sharp photoluminescent emissions limits their application in a variety of water-based applications, such as biological applications. In addition, aqueous solutions can often be very aggressive chemical systems and many of the known water-soluble quantum dots systems degrade, mainly by photoanodic decomposition at the semiconductor surface interface, during long exposure times in water. Thus there remains a need for water-soluble semiconductor nanocrystals which may be prepared as stable, robust suspensions or solutions in aqueous media. There is also a need for water-soluble quantum dots capable of energy emission with high quantum efficiencies, which possess a narrow particle size (and hence with narrow photoluminescence spectral range).

It is the object of the invention to provide water-soluble semiconductor nanocrystals (quantum dots) which overcome the limitations of the prior art and which exhibit high quantum yields with photoluminescence emissions of high spectral purity.

It is yet a further object of the present invention to provide a quantum dot which is readily soluble in aqueous systems and demonstrates chemical and electronic stability therein.

It is yet a further object of the invention to provide a water-soluble quantum dot derivatized to provide linking or coupling capability.

SUMMARY OF THE INVENTION

In one aspect of the invention, a water-soluble semiconductor nanocrystal capable of energy emission is provided. The nanocrystal includes a quantum dot having a selected band gap energy overcoated with a layer of a material having a band gap energy greater than that of the quantum dot and with appropriate band offsets. An outer layer is found at the outer surface of the overcoating layer. The outer layer includes a compound having at least one linking group for attachment of the compound to the overcoating layer and at least one hydrophilic group spaced apart from the linking group by a hydrophobic region sufficient to prevent electron charge transfer across the hydrophobic region.

The outer layer of the nanocrystal may comprise an organic compound. The organic compound may be comprised of moieties selected to provide solubility in an aqueous medium, such as a long chain hydrocarbon terminating in a moiety having affinity for an aqueous medium, and a moiety that demonstrates an affinity to the quantum dot surface. The affinity for the nanocrystal surface promotes coordination of the organic compound to the quantum dot outer surface and the moiety with affinity for the aqueous medium stabilizes the quantum dot suspension.

In preferred embodiments, the compound may have the formula, $H_zX((CH_2)_nCO_2H)_y$ and salts thereof, where X is S, N, P or O=P; $n \geq 6$; and z and y are selected to satisfy the valence requirements of X. In other preferred embodiments, the compound may have the formula,

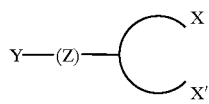

where X and X' are the same or different and are selected from the group of S, N, P or O=P; Y is a hydrophilic moiety; and Z is a hydrophobic region having a backbone of at least six atoms. X and X' may include other substituents in order to satisfy the valence requirements, such as for example, amines, thiols, phosphine and phosphine oxides, substituted by hydrogen or other organic moieties. In addition, the atoms bridging X and X' are selected to form a 5-membered to 8-membered ring upon coordination to the semiconductor surface. The bridging atoms are typically carbon, but may be other elements, such as oxygen, nitrogen, and sulfur. Y may be any charged or polar group, such as carboxylates, sulfonates, phosphates, polyethylene glycol and ammonium salt, and the like. Z is a hydrophobic group, typically an alkyl group or alkenyl group, but may also include other atoms, such as oxygen, sulfur, silicon or nitrogen. Z may be further modified as described herein to provide attractive interactions with neighboring ligands.

In yet another preferred embodiment, the compound may have the formula,

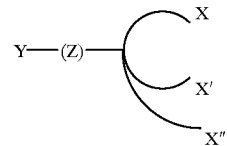

where X, X' and X" are the same or different and are selected from the group of S, N, P or O=P; Y is a hydrophobic moiety; and Z is a hydrophobic region having a backbone of at least six atoms. X, X' and X" may include other substituents in order to satisfy the valence requirements, such as for example, amines, thiols, phosphine and phosphine oxides, substituted by hydrogen or other organic moieties. In addition, the atoms bridging X, X' and X" are selected to form a 5-membered to 8-membered ring upon coordination to the semiconductor surface. The bridging atoms are typically carbon, but may be other elements, such as oxygen, nitrogen, and sulfur. Y may be any charged or polar group, such as carboxylates, sulfonates, phosphates, polyethylene glycol and ammonium salt, and the like. Z is a hydrophilic group, typically an alkyl group or alkenyl group, but may also include other atoms, such as oxygen, sulfur, silicon or nitrogen. Z may be further modified as described herein to provide attractive interactions with neighboring ligands.

In yet another embodiment of the invention, the compound may be a block copolymer. A first block is provided that includes a pendant group capable of functioning as a linking moiety, Y. A second block is provided that includes a pendant group capable of functioning as a hydrophilic group, X. The polymer block serves as a hydrophilic region. In preferred embodiment, the compound may have the formula,

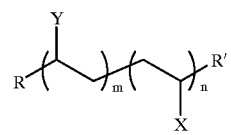

where X are the same or different and elements selected from the group of S, N, P or O=P; and Y is a hydrophilic moiety, such as carboxylates, sulfonates, phosphates, polyethylene glycol and ammonium salt, and the like. X may include other substituents in order to satisfy the valence requirements, such as for example, amines, thiols, phosphine and phosphine oxides, substituted by hydrogen or other organic moieties. The terminal groups R and R' may be any moiety. In particular, it is desirable for R to be a polar moiety due to its proximity to the hydrophilic block. Similarly, it is desirable for R' to be a non-polar moiety due to its proximity to the hydrophobic block. m and n are selected in relation to the number of available coordinating sites on the surface of the quantum dot. It is desirable that m be no greater than the number of available coordinating sites and preferably no greater than one-fourth of available coordinating sites. In typical applications, m is in the range of about 3 to 100. The value of n is typically chosen to be commensurate with the value for m. Thus, it is desirable that n be no greater than the number of available coordinating sites and preferably no greater than one-fourth of available coordinating sites. In typical applications, n is in the range of about 3 to 100.

In another aspect of the invention, a water-soluble semiconductor nanocrystal is provided in which the water solubilizing layer is a bilayer, having a first layer of the bilayer having affinity for the overcoating layer and a second layer of the bilayer having a hydrophobic region adjacent to the first layer and terminating in a hydrophilic group. The bilayer may include a coordinating lyophilic compound used in the manufacture of the semiconductor nanocrystal as the first layer and a surfactant as the second layer.

By "quantum dot" as that term is used herein, it is meant a semiconductor nanocrystal with size-dependent optical and electrical properties. In particular, the band gap energy of a quantum dot varies with the diameter of the crystal. In the naming convention used herein to refer to coated nanocrystals, the compound found within parentheses represents the core compound (i.e. the quantum dot), while the compound which follows represents the overcoated layer. "Quantum yield" as that term is used herein, means the ratio of photons emitted to that absorbed, e.g., the photoluminescence quantum yield.

In other embodiments of the invention, the coated nanocrystal is characterized in that the nanocrystal exhibits less than a 10% and preferably less than 5%, rms deviation in diameter of the core. The nanocrystal in an aqueous environment preferably exhibits photoluminescence having quantum yields of greater than 10%, and most preferably in the range of about 10 to 30%.

Upon exposure to a primary light source, the quantum dot emits energy of a wavelength characteristic of its composition and size. The water-soluble layer of the invention may be used with nanocrystals having various combinations of nanocrystal core and overcoating. The invention permits the preparation of a variety of water-soluble nanocrystals having a very narrow particle size distribution and exhibiting improvements in color purity and intensity of their photoluminescent emissions, as well as demonstrating robustness and stability in water-based suspensions and solutions.

These and other features and advantages of the invention are set forth in the description of the invention, which follows.

BRIEF DESCRIPTION OF THE DRAWING

The invention is described with reference to the figures, which are presented for the purpose of illustration only, and in which.

DETAILED DESCRIPTION OF THE INVENTION

Figure 1:
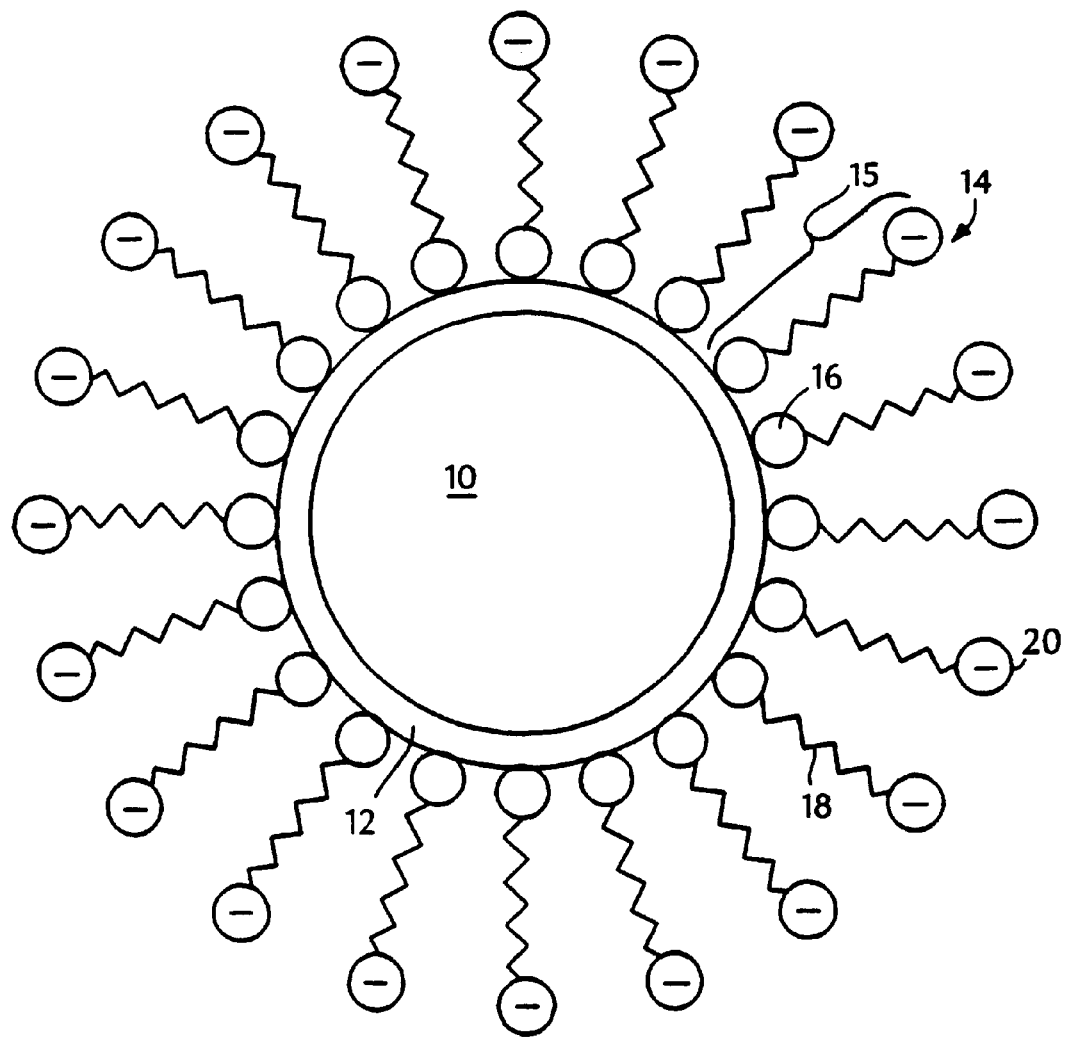
FIG. 1 is a schematic illustration of the water-soluble nanocrystal of the invention.

The present invention is directed to water-soluble semiconductor nanocrystals that are highly luminescent and stable in aqueous solutions. The nanocrystal is represented schematically in FIG. 1. A semiconductor nanocrystal 10 is coated with an outer layer 14 that renders the crystal water-soluble. The outer layer 14 further is selected to maintain the luminescent properties of the nanocrystal and to improve the robustness of the nanocrystal in aqueous solutions. An optional overcoating layer 12 may be used to coat the quantum dot before application of the outer layer 14. The outer layer includes a compound 15 having at least one linking group 16 for attachment of the compound to the overcoating layer and at least one hydrophilic group 20 spaced apart from the linking group by a hydrophobic region 18 sufficient to prevent electron charge transfer across the hydrophobic region. Note that the hydrophobic group 18 is denoted for the sake of convenience as a negative charge in FIG. 1; however, the group may be positively charged or polar neutral.

The nanocrystal includes a semiconductor nanocrystal that demonstrates quantum confinement effects in their luminescent properties. These nanocrystals are known as "quantum dots". When quantum dots are illuminated with a primary energy source, a secondary emission of energy occurs of a frequency that corresponds to the band gap of the semiconductor material used in the quantum dot. In quantum confined particles, the band gap is a function of the size of the nanocrystal.

Most of the II-VI, III-V and group IV semiconductors have been prepared as quantum sized particles and exhibit quantum confinement effects in their physical properties and can be used in the water-soluble nanocrystals of the invention. Exemplary materials suitable for use as quantum dots include ZnS, ZnSe, ZnTe, CdS, CdSe, CdTe, GaN, GaP, GaAs, GaSb, InP, InAs, InSb, AlS, AlP, AlAs, AlSb, PbS, PbSe, Ge, and Si and ternary and quaternary mixtures thereof.

The semiconductor nanocrystals are characterized by their uniform nanometer size. By "nanometer" size, it is meant less than about 150 Angstroms (Å), and preferably in the range of 15–150 Å. The nanocrystal also is substantially monodisperse within the broad size range given above. By monodisperse, as that term is used herein, it is meant a colloidal system in which the suspended particles have substantially identical size and shape. For the purposes of the present invention, monodisperse particles mean that at least 60% of the particles fall within a specified particle size range. In preferred embodiments, monodisperse particles deviate less than 10% in rms diameter, and preferably less than 5%. Monodisperse quantum dots have been described in detail in Murray et al. (*J. Am. Chem. Soc.*, 115:8706 (1993)), the thesis of Christopher Murray, Massachusetts Institute of Technology, September, 1995, supra, and Kuno et al., supra, which are hereby incorporated in their entireties by reference.

In preferred embodiments, the quantum dot has an overcoating layer. At the surface of the quantum dot, surface defects can result in traps for electron or holes that degrade the electrical and optical properties of the quantum dot. An insulating layer at the surface of the quantum dot provides an atomically abrupt jump in the chemical potential at the interface which eliminates energy states that can serve as traps for the electrons and holes. This results in higher efficiency in the luminescent process.

Suitable materials for the overcoating layer include semiconductors having a higher band gap energy than the quantum dot. In addition to having a band gap energy greater than the quantum dots, suitable materials for the overcoating layer should have good conduction and valence band offset with respect to the quantum dot. Thus, the conduction band is desirably higher and the valance band is desirably lower than those of the quantum dot. For quantum dots that emit energy in the visible (e.g., CdS, CdSe, CdTe, ZnSe, ZnTe, GaP, GaAs) or near IR (e.g., InP, InAs, InSb, PbS, PbSe), a material that has a band gap energy in the ultraviolet regions may be used. Exemplary materials include ZnS, GaN, and magnesium chalcogenides, e.g., MgS, MgSe and MgTe. For quantum dots that emit in the near IR, materials having a band gap energy in the visible, such as CdS or CdSe, may also be used. The overcoating layer may include up to eight monolayers of the semiconductor material.

Particularly preferred quantum dots for emission in the visible include CdX, where X=S, Se and Te and ZnY, where Y=Se, Te. For those compounds, ZnS is a preferred material for use as the overcoating. For CdTe, ZnSe may be a preferred material for use as the overcoating due to the higher degree of lattice match between the materials. Overcoated nanocrystals which may be used in the present invention are described in Dabbousi et al. (*J. Phys. Chem. B*, 101(46):9463 (1997)); and Kuno et al., supra; which are hereby incorporated in their entirety by reference.

Most prior art quantum dots are prepared in a coordinating solvent, resulting in the formation of a passivating organic layer on the dot surface comprised of the organic solvent. The passivated quantum dots thus are readily soluble in organic solvents, such as toluene, chloroform and hexane. The present invention provides a surface-modified particle that is soluble instead in aqueous media. According to the invention, the surface of the quantum dot is coated with an outer layer that stabilizes the quantum dot in aqueous solution. The outer layer includes a compound having at least one linking moiety that attaches to the surface of the particle and that terminates in at least one hydrophilic moiety. The linking and hydrophilic moieties are spanned by a hydrophobic region sufficient to prevent charge transfer across the region. The hydrophobic region also provides a "pseudo-hydrophobic" environment for the nanocrystal and thereby shields it from its aqueous surroundings. To exhibit high quantum efficiency it is desirable for the particles to remain electronically isolated from one another. The outer layer of the invention serves the additional useful purpose of maintaining the desired isolation between individual quantum dots.

The outer layer may be made up of any material that meets the structural and performance criteria stated above. The material may be organic or inorganic. In preferred embodiments, the compound is an organic compound. In some embodiments, the outer layer may be made up of a mixture of two or more different water-solubilizing compounds. In other embodiments, the outer layer may comprise additional compounds selected to provide a desirable attribute to the quantum dot. For example, the outer coating may include compounds having reactive functional groups for reaction with other substrates or compounds.

Suitable linking moieties include compounds having electron pairs available for interaction with the semiconductor surface, such as oxygen (O), sulfur (S), nitrogen (N) and phosphine (P). Exemplary compounds include electron-donating compounds such as amines, thiols, phosphines, amine oxides, phosphine oxides, and the like. The linking moiety attaches to the quantum dot surface primarily through coordinate bonding of lone electron pairs of the nitrogen, sulfur, oxygen or phosphorous atom of the linking group. Covalent bonding and ionic bonding may also be used to form the interaction of the outer layer with the semiconductor surface.

Figure 2A:
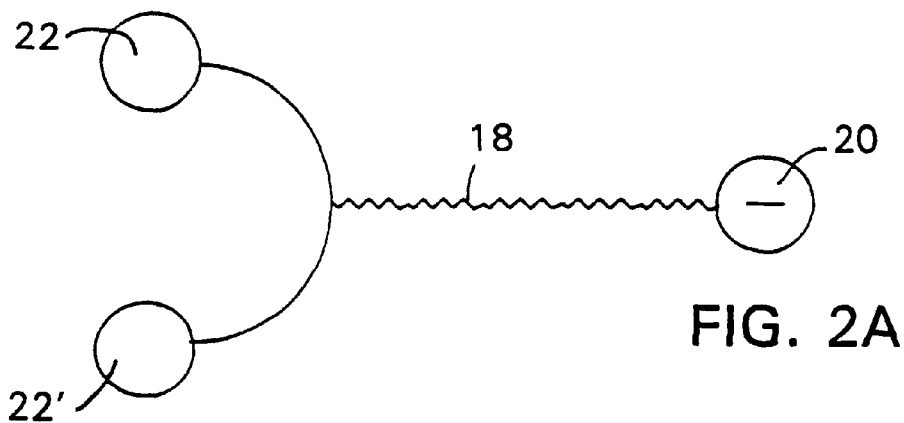
FIG. 2 is a schematic illustration of several alternative embodiments of the water-soluble layer of the nanocrystal.

A compound having a single linking moiety will result in the formation of an outer layer having water-solubilizing properties; however, it may be desirable for the compound to include a plurality of linking moieties, as illustrated schematically in FIG. 2A. Thus, the compound may be a bidentate or tridentate ligand having two or more linking groups 22, 22'. Linking groups as described herein above may be used. For example, the compound may be a derivatized dithiol, diamine, triamine, diphosphine, and the like. The linking groups may be the same or different.

Multidentate ligands provide enhanced stability and robustness to the organic layer and the resulting water-soluble nanocrystal. Without being bound to any particular mode of operation, it is believed that improved stability of the water-soluble nanocrystal is achieved by the increased binding coefficient of the multidentate ligand to the semiconductor surface. Since the organic layer is formed by an exchange reaction with solvated solvent molecules (see below), it follows that the water-solubilizing compound can also be displaced from the surface of the quantum dot. It has been observed for example that the outer layer can be at least partially removed by dialysis of the water-soluble layer. Use of a multidentate ligand increases the strength of the interaction of the compound with the quantum dot and decreases the ease of exchange of the organic layer with other coordinating compounds.

Increased stability of the resultant water soluble quantum dot has been qualitatively observed in the size selective precipitation of coated quantum dots. Quantum dots which have been overcoated with a bidentate ligand such as lipoic acid, exhibit a four-fold increase in suspension stability over a comparable monodentate ligand-coated compound.

The hydrophilic moiety may be a polar or charged (positive or negative) group. The polarity or charge of the group provides the necessary hydrophilic interactions with water to provide stable solutions or suspensions of the quantum dot. Exemplary hydrophilic groups include polar groups such as hydroxides (—OH), alkoxides amines, polyethers, such as polyethylene glycol and the like, as well as charged groups, such as carboxylates (—$CO_2^-$), sulfonates (—$SO_3^-$), phosphates (—$PO_4^{-2}$), and —$PO_3^{2-}$), nitrates, ammonium salts (—$NH_4^+$), and the like.

Figure 2B:
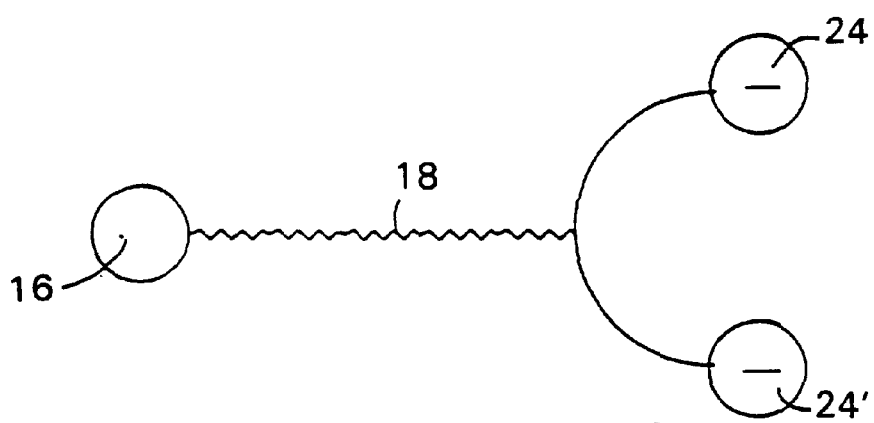
Figure 2C:
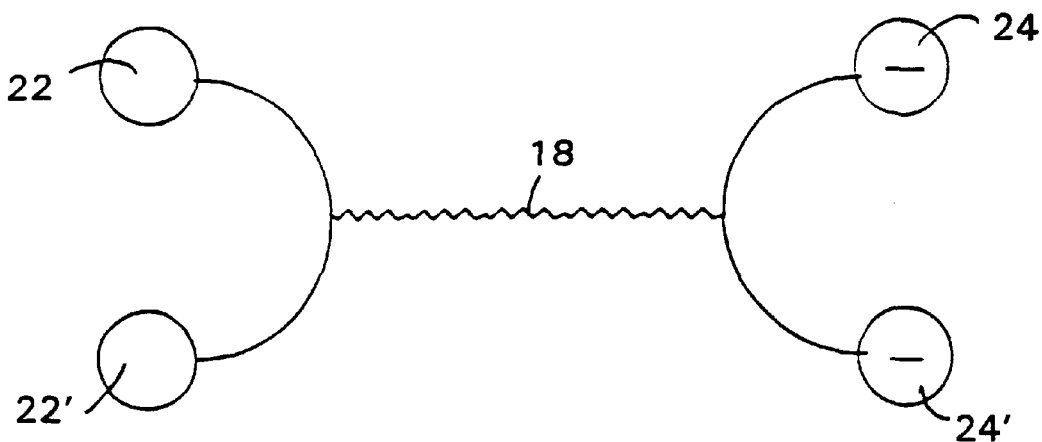

Water-solubility has been achieved using compounds having a single hydrophilic group; however, it may be desirable for the compound to include more than a single hydrophilic moiety, as illustrated schematically in FIG. 2B. FIG. 2B shows a compound having at least two hydrophilic moieties 24, 24'. The hydrophilic groups may be the same or different. It is also contemplated that the water-solubilizing compound may include multiple linking groups and hydrophilic groups, as shown in FIG. 2C.

The hydrophobic region is selected to prevent photooxidation of the surface by charge transfer of a hole to the surface either from the core of the quantum dot or the environment. Typical processes include electrolysis of water from the environment with the resultant oxidation of sulfur or selenium (of the quantum dot) to $SO_2$ or $SeO_2$, in instances where the quantum dot or overcoating layer contains S or Se. Transfer of a charge across the layer represents a non-energy emissive pathway for the excited state of the semiconductor and photoluminescence is thereby significantly reduced or quenched.

Prior art surface modifications of quantum dots includes capping of CdS nanocrystals with 2-mercaptoethanol, 1-thioglycerol and 3-mercaptopropionic acid. See, Lawless et al., supra, and Rogach et al, supra. These short chain organic molecules do not provide a luminescent, water-soluble quantum dot because the short carbon chain does not provide adequate insulation of the quantum dot against photooxidative processes. Therefore, charge transfer occurs between the quantum dot and either the carboxylate or the aqueous environment. Luminescence is quenched and quantum yields are "unacceptably low", i.e., less than 1%, in systems employing short chain organic molecules as a capping layer.

In one embodiment of the invention, the hydrophobic region is a long chain hydrocarbon moiety, $-(CH_2)_n-$, where n is greater than six and preferably greater than eight. Hydrocarbon moieties of n=11 and 15 have been successfully used in the manufacture of the water-soluble nanocrystal of the invention. There is no upper limit to the hydrocarbon chain length; however, it is recognized that very long hydrocarbon chains might render the nanocrystal undesirably "greasy". The hydrophobic region also may include branching hydrocarbons.

In another embodiment, the hydrophobic region may include a modified hydrocarbon backbone. This modification may be the result of coupling reactions, e.g., carbodiimide coupling, used to increase the length of the hydrophobic backbone. Alternatively, non-carbon atoms may be introduced into the backbone to improve the attractive interaction of the water-solubilizing ligand with neighboring compounds.

The backbone also may be modified to include pendant groups that are attractive to neighboring hydrophobic regions through forces such as van der Waals attraction or hydrogen bonding. The attractive interaction between neighboring compounds serves to stabilize the outer layer of the quantum dot. In the event that the linking moiety should dissociate from the semiconductor surface, the attractive interaction with its neighbors will help the compound to remain closely associated with the quantum dot until its linking moiety is able to recoordinate to the surface.

Exemplary modifications include amide, ketone, ether and aromatic moieties, and the like, substituting in whole or in part for the hydrocarbon backbone or attached as pendant groups from the hydrocarbon backbone. The polar nature of the moieties promotes hydrogen bonding and other attractive interaction with neighboring compounds which stabilizes the coating and increases its robustness in aqueous solution.

Figure 3:
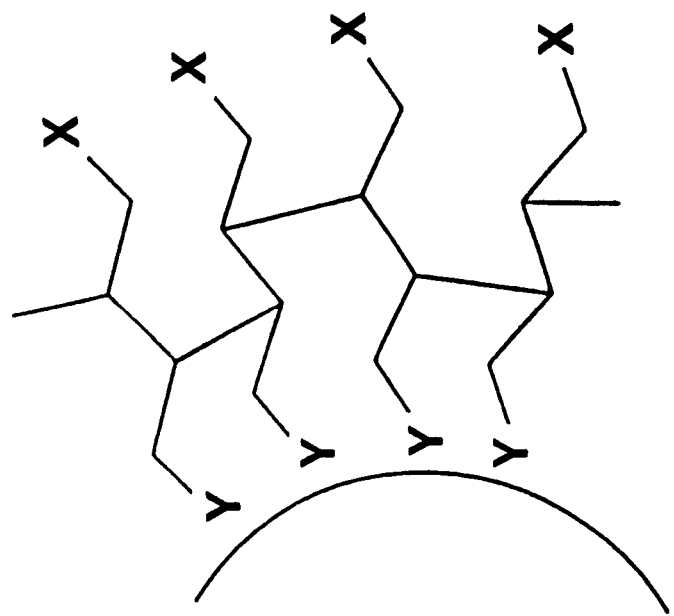
FIG. 3 is an illustration of a water-soluble nanocrystal of the invention having crosslinked hydrocarbon hydrophilic backbone.
Figure 3:
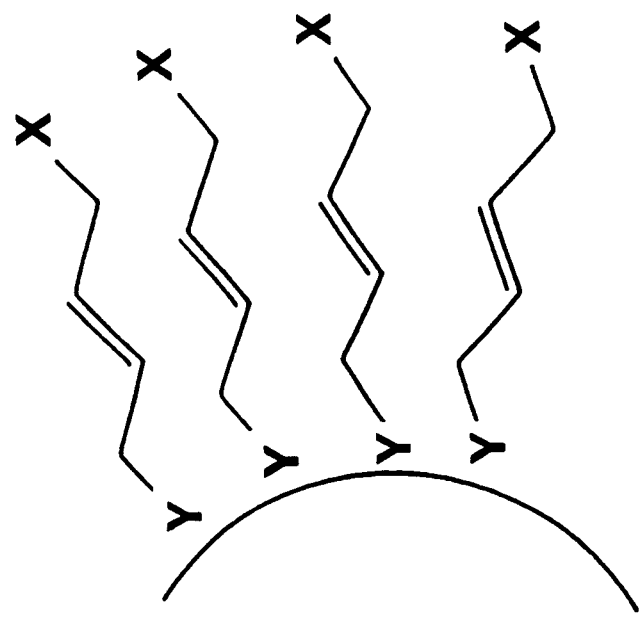

In other embodiments of the invention, the compound of the outer layer is crosslinked to or polymerized with its neighboring compounds. Crosslinking provides stability to the layer by creating an effectively multidentate ligand across the semiconductor surface and significantly reducing ligand volatility and increasing the robustness and stability of the coating. Exemplary crosslinked networks are illustrated schematically in FIG. 3.

To this end, the hydrocarbon chain may include some degree of unsaturation, which may be crosslinked upon exposure to uv energy or other free radical initiator to bridge neighboring ligands. Hydrocarbon unsaturation (and subsequent crosslinks) retain the hydrophobicity desired to prevent the photoinduced degradation of the semiconductor surface.

Figure 4:
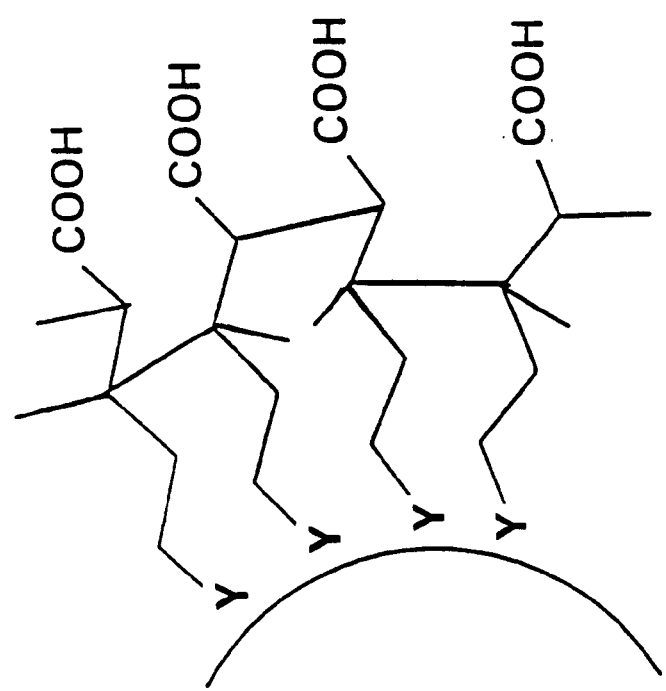
FIG. 4 is an illustration of a water-soluble nanocrystal of the invention comprising a polymethacrylate region.
Figure 4:
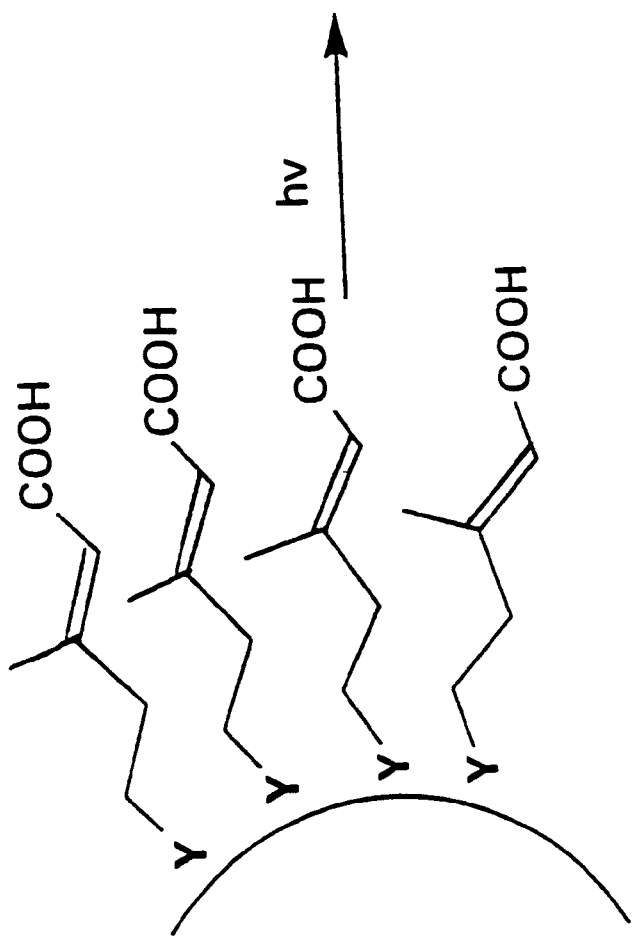

In one embodiment of the invention, the outer layer terminates in an unsaturated hydrophilic moiety that is capable of crosslinking or polymerization. For example, the unsaturated moiety may be acrylic or methacrylate, which may be polymerized by exposure to free radical initiation, heat, uv energy, etc. to form poly(methacrylate), as is shown in FIG. 4. The result is a polymer network, in this example, poly(methacrylate), that interacts with and effectively shields the quantum dot from an aqueous environment. The poly(methacrylate) can be deprotonated to provide a charged surface to render the nanocrystal water soluble. Other exemplary unsaturated moieties for polymerization include acrylic acid and polystyrene derivatized to include a water-solubilizing functional group, e.g., carboxylate and sulfonate, and the like.

In another embodiment of the invention, the outer layer is comprised of a block copolymer that provides the requisite, linking, hydrophilic and hydrophobic functionalities. The copolymer includes at least a first block which contains a pendant group capable of functioning as a linking moiety and a second block having a pendant group capable of functioning as a hydrophilic moiety. The polymer backbone may function as the hydrophobic region. The linking and hydrophilic moieties may be directly attached to the hydrocarbon backbone or they may be attached through intermediary spacing groups. For example, the linking group Z may terminate from an aromatic or alkyl spacing group to provides greater access to the semiconductor surface.

In one embodiment of the invention, the block copolymer may have the formula,

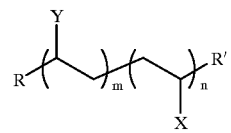

where X and Y are linking moieties and hydrophilic moieties, respectively, and may be any of the moieties discussed hereinabove. The block copolymer may have a molecular weight of 300–50,000. The block sizes for the hydrophilic and linking moieties are preferably in the range of about 3 to 100.

In preferred embodiments, the compound may have the formula, $H_zX((CH_2)_nCO_2H)_y$, and salts thereof, where X is S, N, P or O=P; n≧6; and z and y are selected to satisfy the valence requirements of X. Exemplary compounds for use in the invention may have the formula,

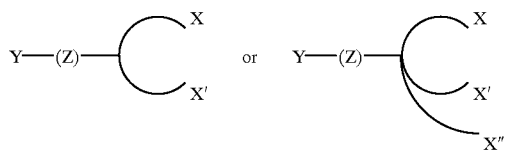

where X, X' and X" are the same or different and are selected from the group of S, N, P or O=P; Y is a hydrophilic moiety; and Z is a hydrophobic region having a backbone of at least six atoms. X, X' and X" may include other substituents in order to satisfy the valence requirements, such as for example, amines, thiols, phosphine and phosphine oxides, substituted by hydrogen or other organic moieties. In addition, the atoms bridging X, X' and X" are selected to form a 5-membered to 8-membered ring upon coordination to the semiconductor surface. The bridging atoms are typically carbon, but may be other elements, such as oxygen, nitrogen, and sulfur. Y may be any charged or polar group, such as carboxylates, sulfonates, phosphates, polyethylene glycol and ammonium salt, and the like. Z is typically an alkyl group or alkenyl group, but may also include other atoms, such as carbon and nitrogen. Z may be further modified as described herein to provide attractive interactions with neighboring ligands.

Exemplary compounds for use in the outer layer of the water-soluble nanocrystal of the invention having the formula provided hereinabove include long chain mercaptocarboxylic acids, $SH(CH_2)_nCOOH$, aminocarboxylic acids, $NH_2(CH_2)_nCOOH$, and phosphinocarboxylic acids, $P((CH_2)_nCOOH)_3$, and their oxides $O=P((CH_2)_nCOOH)_3$, where $n \geq 6$, preferably $n \geq 8$ and more preferably $n=10-12$. The carboxylic acid may be deprotonated to provide the hydrophilic moiety. Other suitable compounds include bidentate ligands, such as, dihydrolipoic acid, $HSCH_2CH_2CH(SH)(CH_2)_4COOH$, or more generally, $HSCH_2CH_2CH(SH)(CH_2)_nCOOH$, where $n=1-10$. The length of the ligand can be increased by standard carbodiimide coupling methods, producing a species with the formula $HSCH_2CH_2CH(SH)(CH_2)_4CONH(CH_2)_nCOOH$. The commercial availability of numerous precursors allows n to be easily varied from 2 to at least 10. Further detail of the carbodiimide coupling reaction may be found in D. H. Rich and J. Singh, *The Peptides* Vol. 1, Academic Press, 1979, 241–2561, which is hereby incorporated by reference.

Other suitable bidentate ligands include the primary amine containing analogues of the above compound, $H_2NCH_2CH_2CH(NH_2)(CH_2)_nCOOH$; derivatives of ethylene diamine, such as $(HOOC(CH_2)_nHNCH_2CH_2NH((CH_2)_nCOOH)$; diphosphines such as $(HOOC(CH_2)_n)_2PCH_2CH_2P((CH_2)_nCOOH)_2$; and the corresponding diphosphine oxides $(HOOC(CH_2)_n)_2P(O)CH_2CH_2P(O)((CH_2)_nCOOH)_2$. An advantage to the use of the above-mentioned carboxylic acid derivatives it that they lend themselves to a wide range of chemistries. For example, the water-soluble quantum dot may be coupled with molecules having biological affinity for use in assaying. In another example, the water-soluble quantum dot may be coupled to beads, solid supports or objects of interest in order to track or identify an article. See co-pending applications filed on even date herewith and entitled "Inventory Control" and application entitled "Detection of Compounds and Interactions in Biological Systems Using Quantum Dots", for further details.

It is readily apparent to one of ordinary skill in the art, that the carboxylic acid moiety of the above-listed compounds may be substituted for a wide variety of charged or polar groups, including but not limited to, hydroxides, polyethers, such as polyethylene glycol and the like, and amines, as well as charged groups, such as carboxylates, sulfonates, phosphates, nitrates, ammonium salts and the like. Compounds such as listed herein above are commercially available or may be synthesized from well-known methods and procedures. It is further apparent that the modifications described above with respect to hydrophobic regions and the hydrophilic groups may be incorporated into the compound described immediately above in preparation of ligands suitable for use in the outer coating of the invention.

Figure 5A:
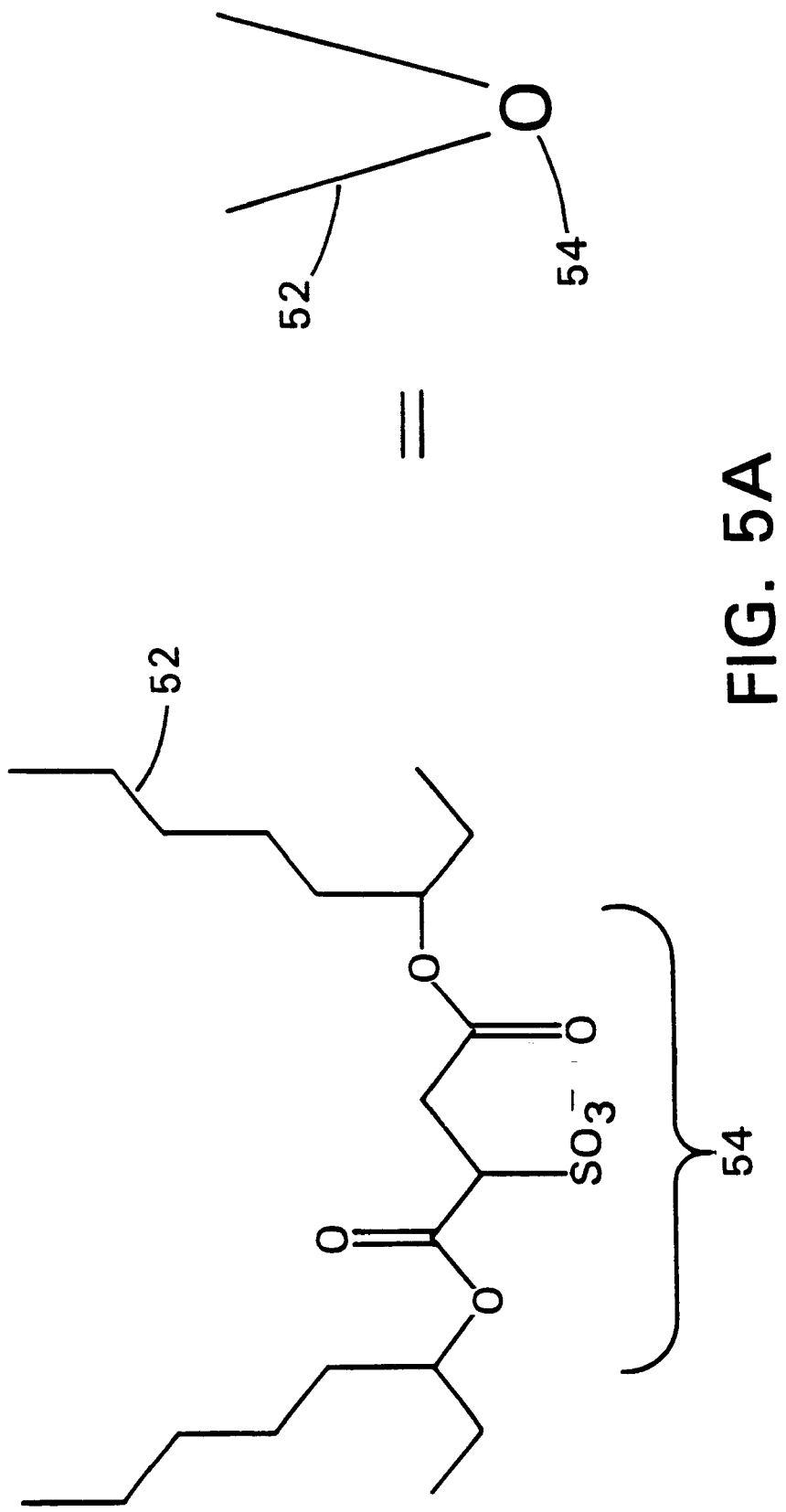
FIG. 5 is a schematic illustration of a bilayer water-soluble nanocrystal of the invention.
Figure 5B:
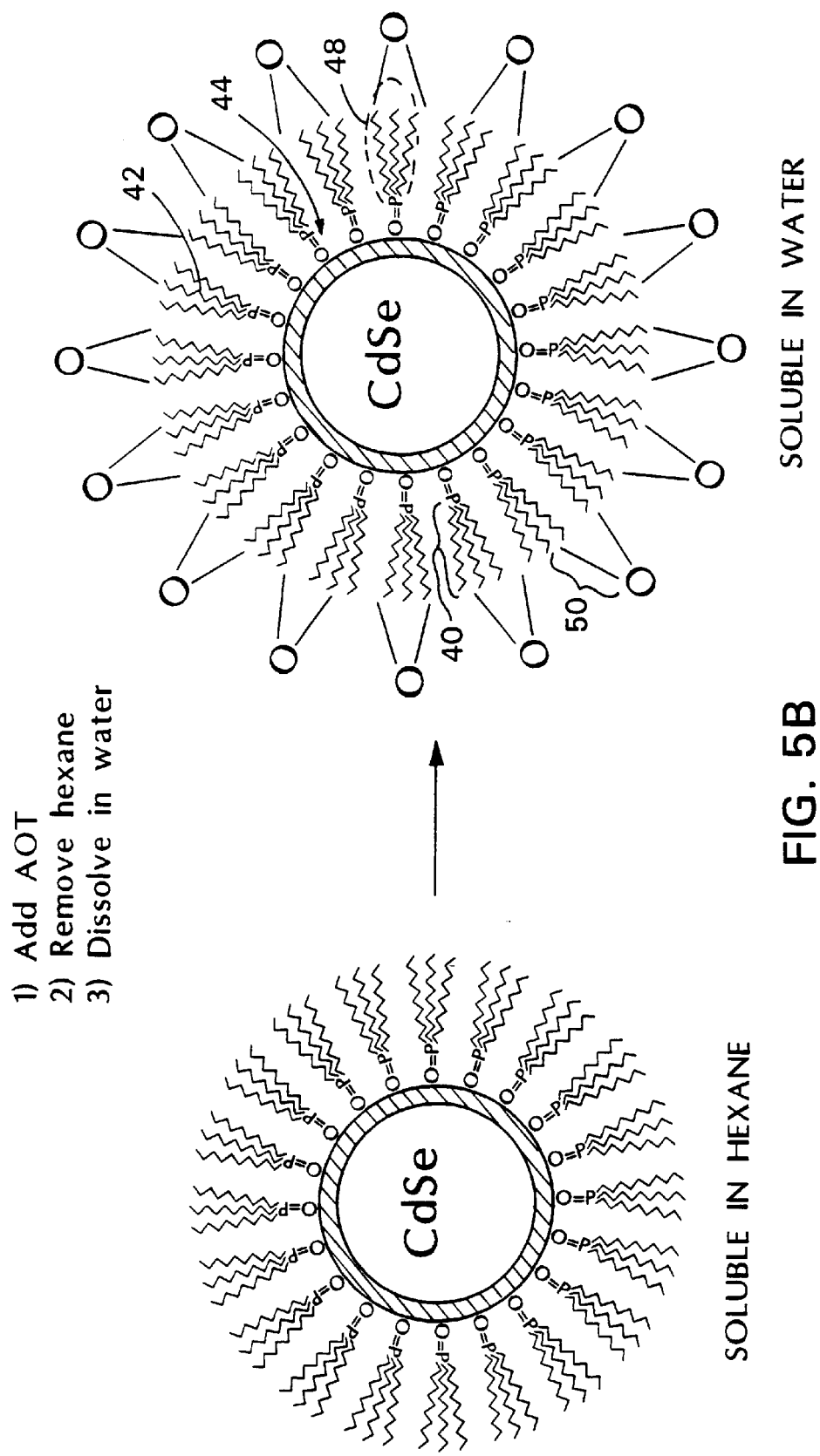

In another aspect of the invention, the water-soluble outer layer may be a bilayer comprising an inner layer having an affinity for the semiconductor surface and an outer layer terminating in a hydrophilic layer having an affinity for an aqueous medium. FIG. 5A illustrates an exemplary compound used in the outer bilayer of the invention. The compound, dioctyl sulfosuccinate (aerosol OT™), contains hydrophobic hydrocarbon regions 52 (denoted schematically as " - - - " in FIG. 5A) and a charged hydrophilic region 54 (denoted by "O" in FIG. 5A). An exemplary bilayer compound is shown in FIG. 5B in which an inner layer 40 includes a compound 42 (here TOPO) having a linking moiety 44 with an affinity for the semiconductor surface. A hydrophobic tail 48 extends from the linking moiety. The second outer layer 50 is comprised of a inner hydrophobic region 52 and an terminal hydrophilic moiety 54 for favorable interaction with an aqueous medium. The hydrophobic regions 48, 52 of the inner and outer layers, respectively, interact preferentially in the aqueous medium, to form a micelle encapsulating the nanocrystal therein. FIG. 5B also illustrates the displacement reaction which occurs to form the bilayer of the invention.

The inner layer may include those coordinating solvents typically used in the manufacture of the quantum dot. Exemplary compounds include trialkyl phosphines and phosphine oxides, such as trioctylphosphine oxide (TOPO), trioctylphosphine (TOP), tributylphosphine (TBP), and the like. Hexadecylamine, an alkylamine is a possible solvent, in particular, for solvating ZnSe.

The second outer layer may include any surfactant having a non-polar tail and a polar head. Non-limiting examples of surfactants include sodium dioctyl sulfosuccinate (known by the trade name AOT soap), $C_{12}H_{25}(OCH_2CH_2)_{23}OH$ (BRIJ 35®) $C_{18}H_{37}(OCH_2CH_2)_{10}OH$ (BRIJ 76®) and $C_{18}H_{37}(OCH_2CH_2)_{20}$ (BRIJ 98®). Even IVORY® soap has been successfully used in the preparation of water-soluble nanocrystals of the invention.

A method for the preparation of the water-soluble nanocrystal follows. The method is described for a (CdSe)ZnS quantum dot, but it is understood that the method may be applied in the preparation of quantum dots from the known semiconductor materials.

A population of nearly monodisperse nanocrystals first is prepared. The actual size of the nanocrystals will vary dependant upon the material used. For CdSe, particles range in size from about 12 Å to about 150 Å with a particle size distribution of about 5–10%. The monodisperse nanocrystals may be obtained by using a high temperature colloidal growth process, optionally followed by size selective precipitation. If spectral emission bandwidths are not as narrow as desired, size selective precipitation may be used to obtain a population of quantum dots of narrower particle size distribution. The interested reader is directed to Murray et al., the thesis of Christopher Murray, and Kuno et al, supra, for further information.

The quantum dot may then be coated with the appropriate semiconductor overcoating layer. The coated nanocrystal may be prepared by introducing the substantially monodisperse first semiconductor nanocrystal and a precursor capable of thermal conversion into a second semiconductor material into a coordinating solvent. The coordinating solvent is maintained at a temperature sufficient to convert the precursor into the second semiconductor material yet insufficient to substantially alter the monodispersity of the first semiconducting nanocrystal and the second semiconductor material has a band gap greater than the first semiconducting nanocrystal. An overcoating of the second semiconductor material is formed on the first semiconducting nanocrystal. The monodispersity of the nanocrystal is monitored during conversion of the precursor and overcoating of the first semiconductor nanocrystal. The particle size distribution may be further refined by size selective precipitation. The coated nanocrystal can emit energy in a spectral range of no greater than about 40 nm at full width half max (FWHM), preferably 30 nm, and more preferably 25 nm. The spectral range of emission can be in the range of about 470 nm to about 650 nm. Further details in the preparation of a coated quantum dot for use in the water-soluble nanocrystal of the invention may be found in U.S. Ser. No. 08/969,302, filed Nov. 13, 1997 and entitled "Highly Luminescent Color-Selective Materials", and Dabbousi et al., supra, which are incorporated in their entirety by reference.

The outer surface of the nanocrystal, as formed, includes an organic layer derived from the coordinating solvent used during the capping layer growth process. The nanocrystal surface may be modified to obtain the water-soluble nanocrystal of the invention by repeated exposure to an excess of a competing coordinating group. For example, a dispersion of the quantum dot may be treated with a coordinating organic compound, such as those described herein, to produce nanocrystals which disperse readily in water, but which no longer disperse in aliphatics. Such a surface exchange process may be carried out using a variety of compounds which are capable of coordinating or bonding to the outer surface of the capped quantum dot, such as by way of example, phosphines, thiols, amines, phosphine oxides and amine oxides.

Figure 6:
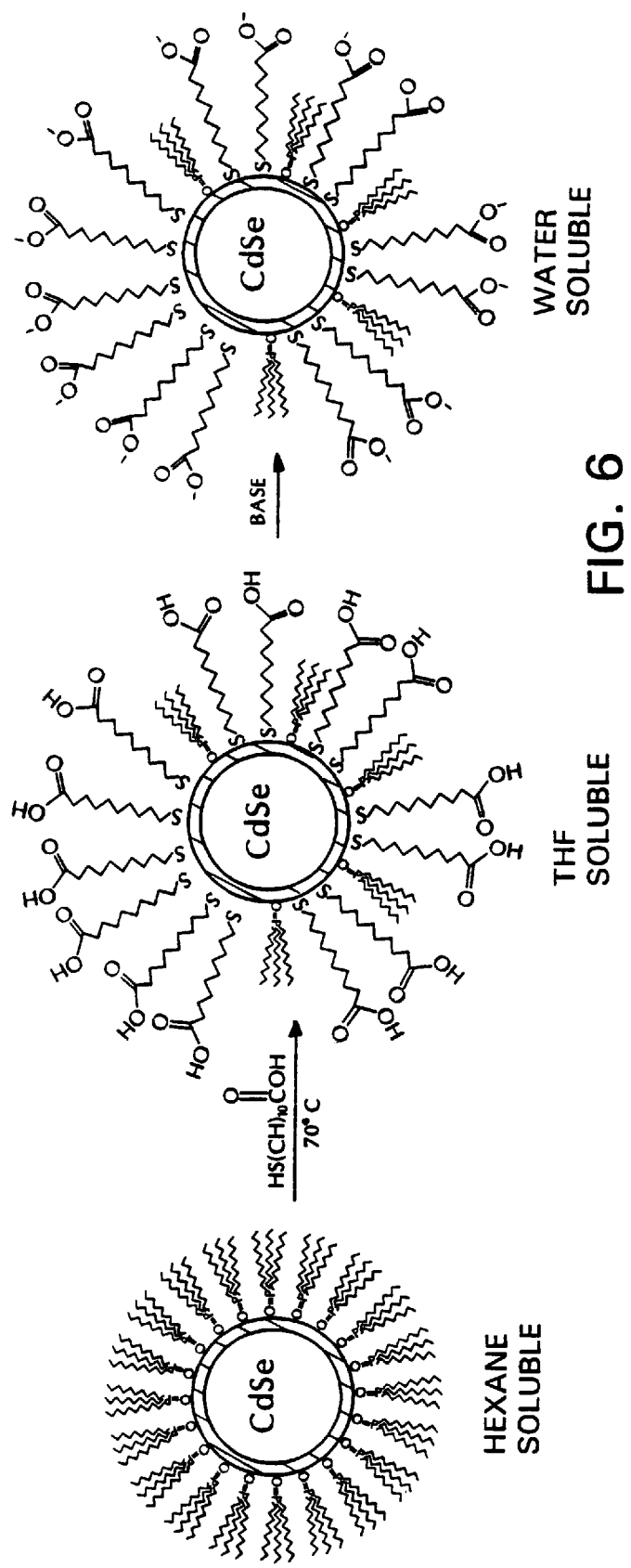
FIG. 6 is an illustration of the displacement reaction used in the formation of the water-soluble nanocrystal of the invention

A typical reaction is shown in FIG. 6. Quantum dots 60 are prepared in a coordinating organic solvent such as trioctylphosphine oxide (TOPO) which results in the formation of a passivating TOPO layer 62 on the semiconductor surface of the quantum dot. This layer is displaced at least in part by the ligand 54, here represented as a long chain mercaptocarboxylic acid, comprising the outer layer of the invention in order to obtain water-soluble nanocrystal 66. Displacement may occur by dispersion of quantum dots or overcoated quantum dots in a medium containing high concentrations of the ligand used to form the outer coating. The medium may be a neat liquid comprising the ligand or it may be a highly concentration solution. High concentrations drive the displacement reaction forward to maximize surface coverage of the nanocrystal by the compound of the outer coating. Note that the displacement of the TOPO layer need not be complete in order to obtain a water-soluble nanocrystal.

It may be desirable to repeatedly expose the nanocrystal to the coordinating ligand solution. The outer coating may be comprised of a mixture of the original polar organic solvent used in the preparation of the nanocrystal and the water-solubilizing compound used in the outer coating of the invention. Substitution of the water-solubilizing compound need only be sufficient to render the compound water-soluble and need not be complete. In some embodiments, substitution is about 25–50% complete, preferably greater than 60% complete. The actual degree of substitution needed for solubility in water will depend on the number of charged or polar groups on the water-solubilizing compound. Higher number of charged or polar groups may require a lower level of surface substitution in order to achieve water solubility.

It is also within the scope of the present invention to include other coordinating ligands on the outer coating of the nanocrystal. The additional ligands may be included to make available additional chemical reactions to the nanocrystal. For example coordinating ligands that terminate in reactive groups such as carboxylic acid, acyl halides and the like may be added to the outer surface of nanocrystal.

The example is illustrated in the following examples, which are presented for the purpose of illustration only and which are not limiting of the invention.

EXAMPLE 1

Preparation of TOPO capped-(CdSe)ZnS (a) Preparation of CdSe. Trioctylphosphine oxide (TOPO, 90% pure) and trioctylphosphine (TOP, 95% pure) were obtained from Strem and Fluka, respectively. Dimethyl cadmium ($CdMe_2$) and diethyl zinc ($ZnEt_2$) were purchased from Alfa and Fluka, respectively, and both materials were filtered separately through a 0.2 $\mu$m filter in an inert atmosphere box. Trioctylphosphine selenide was prepare by dissolving 0.1 mols of Se shot in 100 ml of TOP thus producing a 1M solution of TOPSe. Hexamethyl (disilathiane) ($TMS_2S$) was used as purchased from Aldrich. HPLC grade n-hexane, methanol, pyridine and n-butanol were purchased from EM Sciences.

The typical preparation of TOP/TOPO capped CdSe nanocrystals follows. TOPO (30 g) was placed in a flask and dried under vacuum (~1 Torr) at 180° C. for 1 hour. The flask was then filled with nitrogen and heated to 350° C. In an inert atmosphere drybox the following injection solution was prepared: $CdMe_2$ (200 microliters, 2.78 mmol), 1 M TOPSe solution (4.0 mL, 4.0 mmol), and TOP (16 mL). The injection solution was thoroughly mixed, loaded into a syringe, and removed from the drybox.

The heat was removed from the reaction flask and the reagent mixture was delivered into the vigorously stirring TOPO with a single continuous injection. This produces a deep yellow/orange solution with a sharp absorption feature at 470–500 nm and a sudden temperature decrease to ~240° C. Heating was restored to the reaction flask and the temperature was gradually raised to 260–280° C.

Aliquots of the reaction solution were removed at regular intervals (5–10 min) and absorption spectra taken to monitor the growth of the crystallites. The best samples were prepared over a period of a few hours steady growth by modulating the growth temperature in response to changes in the size distribution, as estimated from the sharpness of the features in the absorption spectra. The temperature was lowered 5–10° C. in response to an increase in the size distribution. Alternatively, the reaction can also be stopped at this point. When growth appears to stop, the temperature is raised 5–10° C. When the desired absorption characteristics were observed, the reaction flask was allowed to cool to ~60° C. and 20 mL of butanol were added to prevent solidification of the TOPO. Addition of a large excess of methanol causes the particles to flocculate. The flocculate was separated from the supernatant liquid by centrifugation; the resulting powder can be dispersed in a variety of organic solvents (alkanes, ethers, chloroform, tetrahydrofuran, toluene, etc.) to produce an optically clear solution.

The powder may be further optimized in an optional size selective precipitation procedure. Nanocrystallites were dispersed in a solution of ~10% butanol in hexane. Methanol was then added dropwise to this stirring solution until opalescence persisted. Separation of supernatant and flocculate by centrifugation produced a precipitate enriched with the largest crystallites in the sample. This procedure was repeated until no further sharpening of the optical absorption spectrum was noted. Size-selective precipitation can be carried out in a variety of solvent/nonsolvent pairs, including pyridine/hexane and chloroform/methanol.

(b) Preparation of (CdSe)ZnS. A flask containing 5 g of TOPO was heated to 190° C. under vacuum for several hours then cooled to 60° C. after which 0.5 mL trioctylphosphine (TOP) was added. Roughly 0.1–0.4 μmols of CdSe dots dispersed in hexane were transferred into the reaction vessel via syringe and the solvent was pumped off.

Diethyl zinc (ZnEt$_2$) and hexamethyldisilathiane ((TMS)$_2$S) were used as the Zn and S precursors, respectively. Particle size distribution for a particular sample was determined by comparison of the optical data to those of known quantum dots of known particle size. The amounts of Zn and S precursors needed to grow a ZnS shell of desired thickness for each CdSe sample was calculated based on the ratio of the shell volume to that of the core assuming a spherical core and shell and taking into account the bulk lattice parameters of CdSe and ZnS. For larger particles the ratio of Zn to Cd necessary to achieve the same thickness shell is less than for the smaller dots. The actual amount of ZnS that grows onto the CdSe cores was generally less than the amount added due to incomplete reaction of the precursors and to loss of some material on the walls of the flask during the addition.

Equimolar amounts of the precursors were dissolved in 2–4 mL TOP inside an inert atmosphere glove box. The precursor solution was loaded into a syringe and transferred to an addition funnel attached to the reaction flask. The reaction flask containing CdSe dots dispersed in TOPO and TOP was heated under an atmosphere of N$_2$. The temperature at which the precursors were added ranged from 140° C. for 23 Å diameter dots to 220° C. for 55 Å diameter dots. When the desired temperature was reached the Zn and S precursors were added dropwise to the vigorously stirring reaction mixture over a period of 5–10 minutes.

After the addition was complete the mixture was cooled to 90° C. and left stirring for several hours. Butanol (5 mL) was added to the mixture to prevent the TOPO from solidifying upon cooling to room temperature. The overcoated particles were stored in their growth solution to ensure that the surface of the dots remained passivated with TOPO. They were later recovered in powder form by precipitating with methanol and redispersing into a variety of solvents including hexane, chloroform, toluene, THF and pyridine.

EXAMPLE 2

Preparation of a Water-soluble Quantum Dots Using Long Chain Mercaptocarboxylic Acid TOPO capped-(CdSe)ZnS quantum dots were prepared as described in Example 1. The overcoated (CdSe)ZnS dots were precipitated from the growth solution using a mixture of butanol and methanol. To obtain the precipitated quantum dots, the solution was centrifuged for 5–10 min, the supernatant was decanted and the residue was washed with methanol (2×).

The residue was weighed. The weight of the TOPO cap was assumed to be 30% of the total weight; and a 30-fold molar excess of the new capping compound, 11-mercaptoundecanoic acid (MUA) was added. The residue and MUA (neat solution) were stirred at 60° C. for 8–12 hours. A volume of tetrahydrofuran (THF) equal to the added MUA was added to the MUA/dot mixture, while the mixture was still hot. A clear solution resulted and the coated quantum dots were stored under THF.

The coated quantum dots are rendered water-soluble by deprotonation of the carboxylic acid functional group of the MUA. The deprotonation was accomplished by adding a suspension of potassium t-butoxide in THF to the MUA-quantum dot/THF solution. A gel resulted, which was then centrifuged and the supernatant liquid was poured off. The residue was washed twice with THF, centrifuged each time and the supernatant liquid poured off. The final residue was allowed to dry in air for 10 minutes. Deionized water (Millipore) was added to the residue until a clear solution formed.

The resultant coated quantum dots were tested for photoluminescent quantum yield. A CdSe quantum dot with a four monolayer coating of ZnS coated as described had an absorption band a 480 nm and a photoluminescent band at 500 nm, with a quantum yield of 12%. A second CdSe quantum dot with a four monolayer coating of ZnS coated as described had an absorption band a 526 nm and a photoluminescent band at 542 nm, with a quantum yield of 18%.

EXAMPLE 3

Preparation of a Water-soluble Quantum Dot Using a Multidentate Ligand

A water-soluble quantum dot was prepared as described in Example 2, except that the bidentate ligand, dihydrolipoic acid was used.

The synthesis of a bidentate dithiol ligand was accomplished via the reduction of the coenzyme lipoic acid. The general procedure was described in I. C. Gunsalus, L. S. Barton, W. Gruber, *J. Am. Chem. Soc.* 78:1763–1766 (1956). Sodium borohydride (1.2 g) was added in 30–50 mg portions to a stirring suspension of lipoic acid (6.0 g) in 117 mL of 0.25 M sodium bicarbonate in 0° C. water. The reaction was stirred for 45 minutes at 0° C., after which 100 mL toluene was added and the mixture was acidified to pH~2 with hydrochloric acid. The toluene layer was collected and saved. The aqueous layer was washed three times with 15 mL toluene. The organic layers were combined, dried with anhydrous magnesium sulfate, filtered, and the solvent removed under vacuum, leaving behind the product dihydrolipoic acid as a yellow oil (yield 80%).

Cap exchange was performed using the same procedure as described for 11-mercaptoundecanoic acid. TOPO capped (CdSe)ZnS quantum dots were precipitated from solution and washed twice with methanol. The remaining powder was dissolved (under nitrogen) at 70° C. in the minimum amount (usually 300–600 mg) of dihydrolipoic acid necessary to produce a clear solution. This mixture was stirred at 70° C. for 6 hours, then stored at room temperature. The dots were rendered water soluble by treatment with potassium t-butoxide in THF, as described for the mercaptocarboxylic acid ligands.

EXAMPLE 4

Preparation of a Water-soluble Quantum Dot Using a Surfactant

TOPO capped-(CdSe)ZnS quantum dots were prepared as described in Example 1. The quantum dots were dissolved in hexane to give a solution which was approximately 0.001–0.01 molar concentration of (CdSe)ZnS dots. Sufficient surfactant sodium dioctylsulfosuccinate (trade name AOT) was added to the mixture to produce a solution which is 5% surfactant by weight (but liquid IVORY® soap also worked). The hexane solvent was evaporated under vacuum. The resulting solid residue dissolved in water to give a clear solution whose quantum yield was approximately the same as the sample (~75% of the original value).

What is claimed is:

1. A water-soluble semiconductor nanocrystal comprising:
   a semiconductor material having a selected band gap energy and being a nanocrystal; and
   an outer layer comprising a multidentate compound having at least two linking groups for attachment of the compound to a surface of the nanocrystal and at least one hydrophilic group spaced apart from the linking group by a hydrophobic region sufficient to prevent electron charge transfer across the hydrophobic region.

2. The water-soluble nanocrystal of claim 1, wherein the hydrophoilic group is a charged or polar group.

3. The water-soluble nanocrystal of claim 1, wherein the hydrophilic group is selected from the group consisting of carboxylic acid, carboxylate, sulfonate, hydroxide, alkoxide, ammonium salt, and phosphate.

4. The water-soluble nanocrystal of claim 1, wherein the compound comprises the formula,

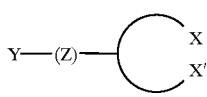

where X and X' are the same or different and are S, N, P or O=P; X and X' may include other substituents in order to satisfy valence requirements; atoms bridging X and X' are selected to form a 5-membered to 8-membered ring upon coordination to the semiconductor surface; Y is a hydrophilic moiety; and Z is a hydrophilic region having a backbone of at least 6 atoms.

5. The water-soluble nanocrystal of claim 1, wherein the compound comprises the formula,

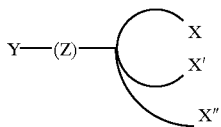

where X, X' and X" are the same or different and are S, N, P or O=P; X, X' and X" may include other substituents in order to satisfy valence requirements; atoms bridging X, X' and X" are selected to form a 5-membered to 8-membered ring upon coordination to the semiconductor surface; Y is a hydrophilic moiety; and Z is a hydrophilic region having a backbone of at least 6 atoms.

6. The water-soluble nanocrystal of claim 1, wherein the compound comprises the formula,

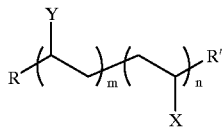

where X is the same or different and is S, N, P or O=P; and X optionally includes other substituents in order to satisfy valence requirements, Y is a hydrophilic moiety, m is in the range about 3 to 200; and n is in the range about 3 to 100, and each of R and R' is an organic moiety.

7. The water-soluble nanocrystal of claim 1, wherein the band gap energy of the semiconductor material is in the near IR energy range.

8. The water-soluble nanocrystal of claim 1, wherein the band gap energy of the semiconductor material is in the visible energy range.

9. The water-soluble nanocrystal of claim 1, wherein the band gap energy of the semiconductor material is in the ultraviolet energy range.

10. The water-soluble nanocrystal of claim 1, wherein the semiconductor material is a member of a substantially monodisperse particle population.

11. The water-soluble nanocrystal of claim 1, wherein the multidentate compound is $HSCH_2CH_2CH(SH)(CH_2)_n COOH$, $H_2NCH_2CH_2CH(NH_2)(CH_2)_nCOOH$, $(HOOC(CH_2)_n)HNCH_2CH_2NH((CH_2)_nCOOH)$, $(HOOC(CH_2)_n)_2PCH_2CH_2P((CH_2)_nCOOH)_2$, $(HOOC(CH_2)_n)_2P(O)CH_2CH_2P(O)((CH_2)_nCOOH)_2$, or $HSCH_2CH_2CH(SH)(CH_2)_4CONH(CH_2)_nCOOH$, where n is from 1 to 10.

12. The water-soluble nanocrystal of claim 1, wherein the multidentate compound is a bidentate compound.

13. The water-soluble nanocrystal of claim 1, wherein the multidentate compound is a tridentate compound.

14. A water-soluble semiconductor nanocrystal comprising:
   a semiconductor material having a selected band gap energy and being a nanocrystal; and
   an outer layer comprising a compound having at least one linking group for attachment of the compound to a surface of the nanocrystal and at least one hydrophilic group spaced apart from the linking group by a hydrophobic region sufficient to prevent electron charge transfer across the hydrophobic region, wherein the compound is crosslinked or polymerized.

15. The water-soluble nanocrystal of claim 14, wherein the hydrophilic group comprises an unsaturated hydrophilic group that is crosslinkable or polymerizable.

16. The water-soluble nanocrystal of claim 15, wherein the unsaturated hydrophilic group is selected from the group consisting of methacrylic acid, acrylic acid, and hydrophilically derivatized styrene.

17. The water-soluble nanocrystal of claim 14, wherein the hydrophobic region is selected from the group consisting of an alkane, an alkene and derivatives thereof modified to include moieties capable of attractive interaction with each other.

18. The water-soluble nanocrystal of claim 14, wherein the outer layer further comprises a plurality of compounds, the hydrophobic regions of adjacent compounds being crosslinked or polymerized to each other.

19. The water-soluble nanocrystal of claim 14, wherein the compound is selected from the group consisting of:
   a compound of the formula, $H_zX((CH_2)_nCO_2H)_y$, and salts thereof, where X is S, N, P or O=P; n≧6; and z and y are selected to satisfy the valence requirements of X;
   a compound of the formula,

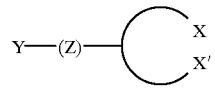

where X and X' are the same or different and are S, N, P or O=P; X and X' optionally includes other substituents in order to satisfy valence requirements; atoms bridging X and X' are selected to form a 5-membered to 8-membered ring upon coordination to the semiconductor surface; Y is a hydrophilic moiety; and Z is a hydrophilic region having a backbone of at least 6 atoms;

a compound of the formula,

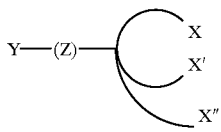

where X, X' and X" are the same or different and are S, N, P or O=P; X, X' and X" optionally includes other substituents in order to satisfy valence requirements; atoms bridging X and X' are selected to form a 5-membered to 8-membered ring upon coordination to the semiconductor surface, atoms bridging X and X" are selected to form a 5-membered to 8-membered ring upon coordination to the semiconductor surface, and atoms bridging X' and X" are selected to form a 5-membered to 8-membered ring upon coordination to the semiconductor surface; Y is a hydrophilic moiety; and Z is a hydrophilic region having a backbone of at least 6 atoms; and a compound of the formula,

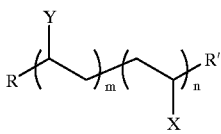

where X is the same or different and is S, N, P or O=P; and X optionally includes other substituents in order to satisfy valence requirements, Y is a hydrophilic moiety, m is in the range about 3 to 200; and n is in the range about 3 to 100, and each of R and R' is an organic moiety.

20. The water-soluble nanocrystal of claim 1, or 14, wherein each linking group independently comprises a moiety selected from the group consisting of amines, thiols, phosphines, phosphine oxides, and amine oxides.

21. The water-soluble nanocrystal of claim 1, or 14, wherein the compound comprises two or more hydrophilic groups.

22. The water-soluble nanocrystal of claim 1, or 14, further comprising a layer overcoating the semiconductor material, between the semiconductor material and the outer layer, the overcoating layer comprised of a material having a band gap energy greater than that of the semiconductor material.

23. A water-soluble semiconductor nanocrystal comprising:
a semiconductor material having a selected band gap energy and being a nanocrystal; and
a bilayer, the bilayer comprising an inner layer having affinity for a surface of the nanocrystal, and an outer layer having a hydrophilic group spaced apart from the inner layer by a hydrophobic region adjacent to the inner layer.

24. The water soluble nanocrystal of claim 23, wherein the inner layer comprises a coordinating lyophilic compound.

25. The water-soluble nanocrystal of claim 24, wherein the coordinating lyophilic compound is selected from the group consisting of a trialkyl phosphine, a phosphine oxide, and an alkyl amine.

26. The water-soluble nanocrystal of claim 25, wherein the coordinating lyophilic compound is tributylphosphine, trioctylphosphine oxide, trioctylphosphine or hexadecylamine.

27. The water soluble nanocrystal of claim 23, wherein the outer layer comprises a surfactant.

28. The water-soluble nanocrystal of claim 27, wherein the surfactant is selected from the group consisting of sodium dioctyl sulfosuccinate, $C_{12}H_{25}(OCH_2CH_2)_{23}OH$, $C_{18}H_{37}(OCH_2CH_2)_{10}OH$, $C_{18}H_{37}(OCH_2CH_2)_{20}OH$, and a sodium salt of fatty acids.

29. The water-soluble nanocrystal of claim 1, 14, 23, wherein the semiconductor material is selected from the group consisting of ZnS, ZnSe, ZnTe, Cds, CdSe, CdTe, GaN, GaP, GaAs, GaSb, InP, InAs, InSb, AlS, AlP, AlAs, AlSb, PbS, PbSe, Ge, and Si and ternary and quaternary mixtures thereof.

30. The water-soluble nanocrystal of claim 1, 14, or 23, wherein when irradiated the nanocrystal emits energy in a spectral range of no greater than about 40 nm full width at half max (FWHM).

31. The water-soluble nanocrystal of claim 1, 14, or 23, wherein the semiconductor material exhibits less than a 10% rms deviation in diameter.

32. The water-soluble nanocrystal of claim 1, 14, or 23, wherein when irradiated the nanocrystal emits energy in a spectral range of no greater than about 30 nm full width at half max (FWHM).

33. The water-soluble nanocrystal of claim 1, 14, or 23, wherein when irradiated the nanocrystal emits energy in a spectral range of no greater than about 25 nm full width at half max (FWHM).

34. The water-soluble nanocrystal of claim 1, 14, or 23, wherein the nanocrystal exhibits photoluminescence having quantum yields of greater than 10% in aqueous medium.

35. The water-soluble nanocrystal of claim 1, 14, or 23, wherein the nanocrystal exhibits photoluminescence having quantum yields in the range of 10–30% in aqueous medium.

36. The water-soluble nanocrystal of claim 1, 14, or 23, wherein the semiconductor material comprises YX, where Y is selected from the group consisting of Zn, Cd, and mixtures thereof and X is selected from the group consisting of S, Se, Te and mixtures thereof.

37. The water-soluble nanocrystal of claim 1, 14, or 23, wherein the nanocrystal has an emission in the range of about 470 nm to about 650 nm.

38. The water-soluble nanocrystal of claim 1, 14, or 23, wherein the particle size of the semiconductor material is selected from the range of about 12 Å to about 150 Å.

39. The water-soluble nanocrystal of claim 22, wherein the overcoating layer is selected from the group consisting of ZnS, ZnSe, CdSe, CdS, GaN, and magnesium chalcogenides.

40. The water-soluble nanocrystal of claim 22, wherein the band gap energy of the overcoating layer is in the ultraviolet energy range.

41. The water-soluble nanocrystal of claim 22, wherein the band gap energy of the overcoating layer is in the visible energy range.

42. The water-soluble nanocrystal of claim 22, wherein the overcoating layer is comprises AB, where A is selected from the group consisting of Zn, Cd, Mg and mixtures thereof and B is selected from the group consisting of S, Se and Te, such that AB is not the same as the semiconductor material and AB has a higher band gap energy than the semiconductor material.

43. A composition, comprising:
a water-soluble nanocrystal including a semiconductor material having a selected band gap energy and being a nanocrystal and an outer layer comprising at least one water-solubilizing moiety selected from the group consisting of a multidentate compound, a bilayer, a crosslinked compound or polymerized compound, the water-solubilizing moiety having at least one linking group for attachment of the compound to the overcoating layer and at least one hydrophilic group spaced apart from the linking group by a hydrophobic region sufficient to prevent electron charge transfer across the hydrophobic region, the water soluble nanocrystal dispersed or dissolved in an aqueous medium.

* * * * *

UNITED STATES PATENT AND TRADEMARK OFFICE
CERTIFICATE OF CORRECTION

PATENT NO.   : 6,251,303 B1
DATED        : June 26, 2001
INVENTOR(S)  : Moungi Bawendi et al.

It is certified that error appears in the above-identified patent and that said Letters Patent is hereby corrected as shown below:

<u>Column 1,</u>
Line 10, please insert the following paragraph:

-- This invention was made with government support under Grant Number DMR-940-0334 awarded by the National Science Foundation. The government may have certain rights in the invention. --

Signed and Sealed this

Twenty-fourth Day of December, 2002

JAMES E. ROGAN
*Director of the United States Patent and Trademark Office*